United States Patent [19]

Hort et al.

[11] 4,361,495

[45] Nov. 30, 1982

[54] REGENERATION OF SUPPORTED-NICKEL CATALYSTS

[75] Inventors: Eugene V. Hort, Wayne; Waldo De Thomas, Parsippany, both of N.J.

[73] Assignee: GAF Corporation, New York, N.Y.

[21] Appl. No.: 243,315

[22] Filed: Mar. 13, 1981

[51] Int. Cl.$^3$ .................. B01J 23/94; B01J 23/92; C07C 29/00

[52] U.S. Cl. .................. 252/411 R; 568/861

[58] Field of Search .................. 252/411 R; 568/861

[56] References Cited

U.S. PATENT DOCUMENTS

| | | | |
|---|---|---|---|
| 3,449,445 | 6/1969 | Wetherill | 568/861 |
| 3,479,411 | 11/1969 | Adam et al. | 568/861 |
| 3,759,845 | 9/1973 | Rudoff et al. | 568/861 |
| 3,926,842 | 12/1975 | Suggitt et al. | 252/411 R |
| 3,950,441 | 4/1976 | Rudoff et al. | 568/861 |
| 4,002,692 | 1/1977 | Mabuchi et al. | 252/414 |

*Primary Examiner*—P. E. Konopka
*Attorney, Agent, or Firm*—James Magee, Jr.; Joshua J. Ward; J. Gary Mohr

[57] ABSTRACT

This invention describes a method of regenerating the activity of deactivated supported-nickel catalysts that have lost activity after use as a hydrogenation catalyst in the finishing stage of the process of conversion of butynediol to butanediol. The method comprises contacting said deactivated catalyst with hydrogen at a temperature of about 200° to 500° C. to convert surface polymers to gaseous compounds and removing said gaseous compounds from the vicinity of the thustreated catalyst. In the preferred form of the invention, in a single step, a slow stream of hydrogen is passed through the deactivated catalyst in situ as a fixed bed and the gaseous compounds are removed simultaneously in the hydrogen stream.

7 Claims, No Drawings

REGENERATION OF SUPPORTED-NICKEL CATALYSTS

BACKGROUND OF THE INVENTION

1. Field of the Invention

This invention relates to a method of regenerating a supported-nickel hydrogenation catalyst used as a finishing catalyst in the conversion of butynediol to butanediol.

2. Description of the Prior Art

In the production of butanediol from butynediol by hydrogenation, butynediol is catalytically hydrogenated to crude butanediol. Then, in a finishing stage, the crude butanediol, which contains a minor amount of partially hydrogenated compounds, including intermediate carbonyl compounds, is again subjected to another catalytic hydrogenation to convert these intermediates to butanediol. The finishing stage is described in detail in U.S. Pat. Nos. 3,950,441; 3,449,445; 3,479,411; and 3,759,845. The result of the multi-stage process is very pure butanediol.

The final stage usually is carried out in a high pressure reactor which is filled with a fixed bed of a supported-nickel catalyst. This catalyst typically comprises about 5 to 50% by weight nickel, and, optionally, one or more promotor metals, such as copper, manganese or molybdenum, usually in an amount of about 1 to 15% by weight of the catalyst. The support is a stable, high-surface-area material, such as alumina or silica. The preferred finishing catalysts for this purpose comprises about 12 to 20% nickel, 1 to 10% copper and 0 to 1.5% manganese.

Upon extended use in the finishing hydrogenation step, the catalyst partly loses its ability to reduce the carbonyl intermediates and other impurities present in the crude butanediol. Generally deactivation of catalyst occurs after processing about 0.5–2.0 thousand pounds of butanediol per pound of catalyst. Thereupon the carbonyl number of the final butanediol product increases, and fresh catalyst must be substituted for deactivated catalyst.

The prior art suggests several alternative methods for regenerating catalysts which have lost activity. However, none of these methods are suitable for use in this system. For example, in U.S. Pat. No. 3,948,991, there is described a sequential method for the removal of a carbonaceous deposit from a deactivated Sn catalyst used in an aldol condensation. The method involves contacting the Sn catalyst in sequence with a carbonyl compound at an elevated temperature and with hydrogen at a higher temperature.

In U.S. Pat. No. 4,098,833, catalysts comprising a metal halide and a Bronsted acid containing fluorine which became deactivated by formation of allyl and alkylaromatic carbonium ion complexes are regenerated with hydrogen at 0° C. to 150° C.

Similarly, in U.S. Pat. No. 3,966,636, a 3-step method is disclosed for regeneration of Rh and Ru catalysts, used for hydrogenation of a carbon to carbon unsaturated bond. The sequence is hydrogenation followed by oxidation followed by hydrogenation. However, oxidation could damage the supported-nickel catalyst of this invention and could lead to local overheating due to its high exotherm.

In U.S. Pat. No. 3,670,041, olefinic unsaturated impurities present in a Pd catalyst from an aromatic-hydrocarbon-deactivated feed are selectively hydrogenated by contact with hydrogenated naphthalene and hydrogen. However, the presence of hydrogenated naphthalene would introduce impurities into the system of this invention.

As seen, for one or more reasons, the prior art methods are not suitable for supported-nickel catalysts used for second stage hydrogenation of crude butanediol. In particular, such catalysts lose activity due to the formation of carbonaceous polymers which are unreactive materials. Nickel catalysts which are supported on a porous support in a fixed bed are quite susceptible to localized heating effects on oxidation, leading to damage to the metal itself.

Accordingly, it is an object of this invention to provide a novel and useful method for regenerating the activity of a deactivated supported nickel catalyst that has lost activity due to the formation of carbonaceous polymers on its catalytic surfaces.

A further object of this invention is to provide a method of restoring substantially all the activity of a deactivated supported-nickel hydrogenation catalyst in situ in a fixed bed.

Another object herein is to provide an efficient, one-step flow process for regenerating a supported-nickel hydrogenation catalyst.

These and other objects and features of the invention will be made apparent from the following description thereof.

SUMMARY OF THE INVENTION

What is provided herein is a novel and useful method of regenerating the activity of a deactivated supported-nickel hydrogenation catalyst that has lost activity due to the formation of carbonaceous polymers on its catalytic surfaces. The method of the invention comprises contacting the deactivated catalyst with hydrogen at a temperature of about 200° to 500° C. to convert the polymers to gaseous carbon compounds and removing the gaseous compounds from the vicinity of the thus-treated catalyst. In the preferred form of the invention, in a single step, a slow stream of hydrogen is passed through the deactivated catalyst in situ as a fixed bed and the gaseous compounds are removed simultaneously in the hydrogen stream.

DETAILED DESCRIPTION OF THE INVENTION

The hydrogen treatment on the deactivated catalyst suitably is carried out at a temperature of about 200° to 500° C., preferably 275° to 375° C., and, in the best mode, at about 300°–350° C.

The hydrogen pressure is not critical and may be atmospheric or higher pressures; up to 300 lbs. per square inch or more may be used.

The process is continued for a period of time which is sufficient to cause a substantial regeneration of the deactivated catalyst. Generally, at least 2 hours, and preferably 12 to 48 hours, to required to restore substantially all of the activity.

While hydrogen itself is the preferred gas, it may be diluted with an inert gas, such as nitrogen.

The following examples will illustrate the invention more particularly.

The efficacy of the regeneration process of the invention is measured by the restoration of the porosity of the catalyst, by increase in its surface area, by decrease in carbon content, and by increased ability to reduce the carbonyl number of the final butanediol product. Ideally, a regenerated catalyst should approximate a new catalyst in activity and lifetime.

EXAMPLE 1

After processing 500 pounds of butanediol per pound of catalyst in the finishing stage of the conversion of butynediol to butanediol, a new supported-nickel catalyst lost much of its ability to reduce carbonyls and color-forming impurities. Two samples of catalyst were tested, one the new catalyst and the other the used catalyst. Part of the used catalyst was washed with water to remove butanediol, other organics, and soluble inorganic salts. Physical properties and elemental analysis were obtained on both the used (washed and dried) and the new catalysts. The results are summarized in Table I.

TABLE I

| Property | New Catalyst | Used Catalyst |
|---|---|---|
| Surface Area, $M^2/g$ | 175 | 142 |
| Pore Volume, cc/g. | 0.52 | 0.16 |
| Carbon, % | 0.65 | 1.60 |
| Hydrogen, % | 0.46 | 1.47 |
| % Nickel | 16.9 | 14.2 |
| % Copper | 5.8 | 4.9 |
| % Manganese | 0.58 | 0.46 |
| % Silica | 0.08 | 1.10 |
| % Magnesium | 0.01 | 0.26 |
| % Sodium | 0.02 | 0.14 |
| % Calcium | 0.05 | 0.02 |
| % Iron | 0.03 | 0.03 |

The surface area and particularly the pore volume of the used catalyst was much lower than that of the new catalyst. The elemental analysis showed major increases in carbon, hydrogen, and silica, with minor increases in magnesium and sodium content.

EXAMPLE 2

Both the new and used catalysts were treated with a flow of hydrogen at 400° C. for 15 hours at atmospheric pressure and analyzed for surface area, pore volume distribution, and carbon and hydrogen content. The results are summarized in Table II.

TABLE II

| Property | New Catalyst | New Catalyst Reduced at 400° C./15 hrs | Used Catalyst | Used Catalyst Reduced at 400° C./15 hrs |
|---|---|---|---|---|
| Surface Area, $M^2/g$. | 175 | 194 | 142 | 191 |
| Total Pore Vol., cc/g. | 0.52 | 0.48 | 0.16 | 0.35 |
| % Carbon | 0.66 | 0.66 | 1.60 | 0.75 |
| % Hydrogen | 0.46 | 0.45 | 1.47 | 0.62 |
| Pore Vol. Distribution cc/g. | | | | |
| up to 120A | 0.260 | 0.253 | 0.095 | 0.195 |
| 120A to 177A | 0.027 | 0.035 | 0.013 | 0.025 |
| 177A to 354A | 0.047 | 0.044 | 0.011 | 0.023 |
| 354A to 884A | 0.063 | 0.054 | 0.019 | 0.023 |
| 884A to 1768A | 0.051 | 0.049 | 0.006 | 0.020 |
| 1768A to 8840A | 0.032 | 0.022 | 0.003 | 0.025 |
| 8840A to 17,680A | 0.002 | 0.003 | 0.000 | 0.000 |
| 17,680A to 121,000A | 0.004 | 0.008 | 0.000 | 0.008 |
| >121,000A | 0.025 | 0.014 | 0.017 | 0.029 |

The pore volume distribution of Table II shows that the small pores (<120 Å) of the used catalyst are blocked in comparison to the new catalyst. After treatment most of these pores have again become available. The reason for this improvement is seen in the carbon and hydrogen analysis which shows that regeneration by hydrogenation removes most of the removable carbon and hydrogen content of the catalyst.

The non-removable carbon in new catalyst originates mostly from the graphite lubricant used during the tableting process. The carbon in the used catalyst has been lowered to almost the same level by the regeneration process. Since the silica, cannot be removed by this process, the reopening of pores and increased surface area are due to the removal of this carbon.

EXAMPLE 3

In this example, the activity of both new and used catalyst was evaluated after treatment with hydrogen. The activity was measured in use in an autoclave under established procedures for the second stage, high pressure hydrogenation of crude butanediol. The following Table III summarizes the experimental results.

TABLE III

Autoclave Series (1) - Hydrogenation Activity

| | Carbonyl Numbers | | |
|---|---|---|---|
| Run No. | New Catalyst | Deactivated Catalyst | Regenerated Catalyst (2) |
| 1 | 0.43 | 2.6 | 0.52 |
| 2 | 0.36 | 3.3 | 0.56 |
| 3 | 0.40 | 3.1 | 0.59 |
| 4 | 0.42 | 2.7 | 0.56 |

(1) Crude butanediol Feed, Carbonyl Number 27; Hydrogenation conditions: Temp. 140° C., Press. 2000 psig, time 6 hrs.
(2) Reduction by 400° C./15 hrs. at atm. pressure The results show that the regenerated catalyst had activity almost equal to the new catalyst. Analysis of the product solution from the fourth run of this series gave the following results. The used catalyst gave product purity almost equivalent to that from the new catalyst.

TABLE IV

| Catalyst | % BuOH | % HBA | % BID | % MBID | % Acetal | % MPID | % HID |
|---|---|---|---|---|---|---|---|
| New | 1.55 | Trace | 96.3 | 0.64 | Trace | 0.21 | 0.06 |
| Used | 1.73 | Trace | 95.5 | 0.88 | Trace | 0.24 | 0.03 |

BuOH—butanol
HBA—hydroxybutyraldehyde
BID—butanediol
MBID—methylbutanediol
MPID—methylpentanediol
HID—hexanediol
Acetal—HBA—BID acetal

EXAMPLE 4

The regeneration process was carried out in situ using a flow of hydrogen at atmospheric pressure for a period of 6 hours through the fixed bed supported-nickel catalyst of Example 1 maintained at 350° C. The catalyst had become deactivated after operating as the final stage catalyst and processing about 1000 lbs. of feed per lb. of catalyst. The results of using the catalyst are shown in Table V below.

TABLE V

| | Carbonyl Number | | |
|---|---|---|---|
| Run No. | New Catalyst | Used Catalyst | Regenerated Catalyst |
| 1 | 0.28 | 2.1 | 0.22 |
| 2 | 0.18 | 2.3 | 0.22 |
| 3 | 0.26 | 2.7 | 0.27 |
| 4 | 0.29 | 2.8 | 0.27 |

The results show complete restoration of activity of the used catalyst to that of new catalyst.

While the invention has been described with particular reference to certain embodiments thereof, it will be understood that changes and modifications may be made which are within the skill of the art. Accordingly, it is intended to be bound only by the appended claims, in which.

What is claimed is:

1. A method of regenerating the activity of a deactivated supported-nickel catalyst that has lost activity due to the formation of carbonaceous polymers on its catalytic surfaces while in use as a hydrogenation catalyst in the finishing stage of the process of conversion of butynediol to butanediol, said catalyst consisting essentially of, in percent by weight, about 5 to 50% nickel, and, optionally, about 1 to 15% of one or more promotor metals selected from the group consisting of copper, manganese and molybdenum, which comprises:
    contacting said deactivated catalyst with hydrogen at a temperature of about 200° to 500° C. to convert said polymers to gaseous carbon compounds and removing said gaseous compounds from the vicinity of the thus-treated catalyst.

2. A method according to claim 1 wherein said temperature is about 275° to 375° C.

3. A method according to claim 1 wherein said deactivated catalyst is contacted in situ with a flow of hydrogen and said gaseous compounds are removed simultaneously in said flow.

4. A method according to claim 3 wherein said catalyst is present in a fixed bed.

5. A method according to claim 4 wherein said catalyst is supported on a highly porous silica or alumina support.

6. A method according to claim 4 wherein said catalyst consists essentially of about 12 to 20% nickel, about 1 to 10% copper and about 0.1 to 1.5% manganese.

7. A method according to claim 4 wherein said deactivated catalyst is contacted with hydrogen for at least 2 hours.

* * * * *